United States Patent
Belcheva

(10) Patent No.: US 9,247,931 B2
(45) Date of Patent: Feb. 2, 2016

(54) MICROWAVE-POWERED REACTOR AND METHOD FOR IN SITU FORMING IMPLANTS

(75) Inventor: Nadya Belcheva, Essex Junction, VT (US)

(73) Assignee: Covidien LP, Mansfield, MA (US)

( * ) Notice: Subject to any disclaimer, the term of this patent is extended or adjusted under 35 U.S.C. 154(b) by 407 days.

(21) Appl. No.: 13/807,788

(22) PCT Filed: Jun. 29, 2011

(86) PCT No.: PCT/US2011/042336
§ 371 (c)(1),
(2), (4) Date: May 3, 2013

(87) PCT Pub. No.: WO2012/006147
PCT Pub. Date: Jan. 12, 2012

(65) Prior Publication Data
US 2013/0211448 A1      Aug. 15, 2013

Related U.S. Application Data

(60) Provisional application No. 61/359,552, filed on Jun. 29, 2010.

(51) Int. Cl.
*A61B 17/00* (2006.01)
*A61L 24/04* (2006.01)
*A61L 31/04* (2006.01)

(52) U.S. Cl.
CPC ........... *A61B 17/0057* (2013.01); *A61L 24/043* (2013.01); *A61L 31/041* (2013.01); *A61B 2017/005* (2013.01); *A61B 2017/00495* (2013.01); *A61B 2017/00685* (2013.01)

(58) Field of Classification Search
CPC .. A61L 31/04; A61L 24/043; A61B 17/0057; A61B 2017/00495; A61B 2017/00685; A61B 2017/005
See application file for complete search history.

(56) References Cited

U.S. PATENT DOCUMENTS

| 3,494,359 A | 2/1970 | Zackheim |
| 3,767,085 A | 10/1973 | Cannon et al. |

(Continued)

FOREIGN PATENT DOCUMENTS

| BE | 1008260 A6 | 2/1996 |
| EP | 0077098 A2 | 4/1983 |

(Continued)

OTHER PUBLICATIONS

Q. Shi, et al., "The Immobilization of Proteins on Biodegradable Polymer Fibers via Click Chemistry", Biomaterials, 29, (2008), pp. 1118-1126.

(Continued)

*Primary Examiner* — Kishor Mayekar

(57) ABSTRACT

The present disclosure relates to an apparatus and process for forming medical devices from an injectable composition. The apparatus includes a supply assembly, a mixing assembly, and at least one source of microwave energy. The supply assembly is configured to maintain and selectively dispense a first precursor functionalized with a first reactive member and a second precursor functionalized with a second reactive member. The mixing assembly is configured to mix the first and second precursors within a mixing cavity defined therein. The microwave energy source is configured and adapted to irradiate the mixed first and second precursors within the mixing cavity.

15 Claims, 4 Drawing Sheets

(56) References Cited

U.S. PATENT DOCUMENTS

| | | | |
|---|---|---|---|
| 4,326,532 A | 4/1982 | Hammar | |
| 4,359,049 A | 11/1982 | Redl et al. | |
| 4,464,321 A | 8/1984 | Pittalis et al. | |
| 4,538,920 A | 9/1985 | Drake | |
| 4,604,215 A * | 8/1986 | McCorquodale | 210/762 |
| 4,753,536 A | 6/1988 | Spehar et al. | |
| 4,839,345 A | 6/1989 | Doi et al. | |
| 4,857,403 A | 8/1989 | De Lucca et al. | |
| 4,880,662 A | 11/1989 | Habrich et al. | |
| 4,898,580 A | 2/1990 | Crowley | |
| 4,915,695 A | 4/1990 | Koobs | |
| 5,021,207 A | 6/1991 | De Lucca et al. | |
| 5,104,375 A | 4/1992 | Wolf et al. | |
| 5,372,585 A | 12/1994 | Tiefenbrun et al. | |
| 5,455,308 A | 10/1995 | Bastiaansen | |
| 5,562,946 A | 10/1996 | Fofonoff et al. | |
| 5,578,662 A | 11/1996 | Bennett et al. | |
| 5,582,955 A | 12/1996 | Keana et al. | |
| 5,612,050 A | 3/1997 | Rowe et al. | |
| 5,685,846 A | 11/1997 | Michaels, Jr. | |
| 5,804,318 A | 9/1998 | Pinchuk et al. | |
| 5,911,942 A | 6/1999 | Fofonoff et al. | |
| 5,916,585 A | 6/1999 | Cook et al. | |
| 5,935,437 A | 8/1999 | Whitmore | |
| 5,971,953 A | 10/1999 | Bachynsky | |
| 6,099,563 A | 8/2000 | Zhong | |
| 6,107,365 A | 8/2000 | Bertozzi et al. | |
| 6,107,453 A | 8/2000 | Zuccato et al. | |
| 6,312,725 B1 | 11/2001 | Wallace et al. | |
| 6,342,591 B1 | 1/2002 | Zamora et al. | |
| 6,406,455 B1 | 6/2002 | Willis et al. | |
| 6,451,032 B1 | 9/2002 | Ory et al. | |
| 6,534,611 B1 | 3/2003 | Darling et al. | |
| 6,552,103 B1 | 4/2003 | Bertozzi et al. | |
| 6,570,040 B2 | 5/2003 | Saxon et al. | |
| 6,576,000 B2 | 6/2003 | Carrison | |
| 6,624,245 B2 | 9/2003 | Wallace et al. | |
| 6,805,876 B2 | 10/2004 | Leong et al. | |
| 6,881,766 B2 | 4/2005 | Hain | |
| 6,958,212 B1 | 10/2005 | Hubbell et al. | |
| 7,012,126 B2 | 3/2006 | Matsuda et al. | |
| 7,105,629 B2 | 9/2006 | Matsuda et al. | |
| 7,122,703 B2 | 10/2006 | Saxon et al. | |
| 7,144,976 B2 | 12/2006 | Matsuda et al. | |
| 7,172,877 B2 | 2/2007 | Ting | |
| 7,247,692 B2 | 7/2007 | Laredo | |
| 7,294,357 B2 | 11/2007 | Roby | |
| 7,371,719 B2 | 5/2008 | Stupp et al. | |
| 7,375,234 B2 | 5/2008 | Sharpless et al. | |
| 7,560,588 B2 | 7/2009 | Breitenkamp et al. | |
| 7,618,944 B2 | 11/2009 | Breitenkamp et al. | |
| 7,638,558 B2 | 12/2009 | Breitenkamp et al. | |
| 7,650,588 B2 | 1/2010 | Ivansen | |
| 7,667,012 B2 | 2/2010 | Saxon et al. | |
| 7,795,355 B2 | 9/2010 | Matyjaszewski et al. | |
| 7,807,619 B2 | 10/2010 | Bertozzi et al. | |
| 7,981,444 B2 | 7/2011 | Tomalia et al. | |
| 7,985,424 B2 | 7/2011 | Tomalia et al. | |
| 8,034,396 B2 | 10/2011 | Kapiamba et al. | |
| 2002/0016003 A1 | 2/2002 | Saxon et al. | |
| 2002/0161170 A1 | 10/2002 | Matsuda et al. | |
| 2002/0169275 A1 | 11/2002 | Matsuda et al. | |
| 2002/0173616 A1 | 11/2002 | Matsuda et al. | |
| 2003/0100086 A1 | 5/2003 | Yao et al. | |
| 2003/0109866 A1 | 6/2003 | Edwards et al. | |
| 2003/0109886 A1 | 6/2003 | Keegan et al. | |
| 2003/0135238 A1 | 7/2003 | Milbocker | |
| 2003/0162903 A1 | 8/2003 | Day | |
| 2003/0199084 A1 | 10/2003 | Saxon et al. | |
| 2003/0205454 A1 | 11/2003 | Hlavinka et al. | |
| 2004/0170752 A1 | 9/2004 | Luthra et al. | |
| 2004/0185053 A1 | 9/2004 | Govindan | |
| 2004/0209317 A1 | 10/2004 | Ting | |
| 2004/0249438 A1 | 12/2004 | Lefranc et al. | |
| 2005/0032081 A1 | 2/2005 | Ju et al. | |
| 2005/0038472 A1 | 2/2005 | Furst | |
| 2005/0148032 A1 | 7/2005 | Saxon et al. | |
| 2005/0185508 A1 * | 8/2005 | Schulz-Hanke et al. | 366/336 |
| 2005/0222427 A1 | 10/2005 | Sharpless et al. | |
| 2005/0233389 A1 | 10/2005 | Ting et al. | |
| 2005/0244453 A1 | 11/2005 | Stucke et al. | |
| 2006/0018948 A1 | 1/2006 | Guire et al. | |
| 2006/0025815 A1 | 2/2006 | McGurk et al. | |
| 2006/0036022 A1 | 2/2006 | Callaghan et al. | |
| 2006/0050262 A1 | 3/2006 | Poon et al. | |
| 2006/0085033 A1 | 4/2006 | Criscuolo et al. | |
| 2006/0108393 A1 | 5/2006 | Heinrich et al. | |
| 2006/0110782 A1 | 5/2006 | Bertozzi et al. | |
| 2006/0142404 A1 | 6/2006 | Berge et al. | |
| 2006/0147963 A1 | 7/2006 | Barone et al. | |
| 2006/0189944 A1 | 8/2006 | Campbell et al. | |
| 2006/0193865 A1 | 8/2006 | Govindan | |
| 2006/0228300 A1 | 10/2006 | Chang et al. | |
| 2006/0228357 A1 | 10/2006 | Chang et al. | |
| 2006/0240092 A1 | 10/2006 | Breitenkamp et al. | |
| 2006/0276658 A1 | 12/2006 | Saxon et al. | |
| 2007/0005020 A1 | 1/2007 | Laveault | |
| 2007/0020620 A1 | 1/2007 | Finn et al. | |
| 2007/0037964 A1 | 2/2007 | Saxon et al. | |
| 2007/0060658 A1 | 3/2007 | Diaz et al. | |
| 2007/0077564 A1 | 4/2007 | Roitman et al. | |
| 2007/0086942 A1 | 4/2007 | Chang et al. | |
| 2007/0087001 A1 | 4/2007 | Taylor et al. | |
| 2007/0099251 A1 | 5/2007 | Zhang et al. | |
| 2007/0118211 A1 | 5/2007 | Gazza | |
| 2007/0140966 A1 | 6/2007 | Chang et al. | |
| 2007/0178133 A1 | 8/2007 | Rolland | |
| 2007/0178448 A1 | 8/2007 | Tsao et al. | |
| 2007/0190597 A1 | 8/2007 | Agnew et al. | |
| 2007/0212267 A1 | 9/2007 | Organ et al. | |
| 2007/0244265 A1 | 10/2007 | Matyjaszewski et al. | |
| 2007/0244296 A1 | 10/2007 | Tomalia et al. | |
| 2007/0249014 A1 | 10/2007 | Agnew et al. | |
| 2007/0254006 A1 | 11/2007 | Loose et al. | |
| 2007/0258889 A1 | 11/2007 | Douglas et al. | |
| 2007/0269369 A1 | 11/2007 | Gegg et al. | |
| 2007/0272122 A1 | 11/2007 | Lahann et al. | |
| 2007/0275387 A1 | 11/2007 | Ju | |
| 2007/0298006 A1 | 12/2007 | Tomalia et al. | |
| 2008/0015138 A1 | 1/2008 | Hamilton et al. | |
| 2008/0021486 A1 | 1/2008 | Oyola et al. | |
| 2008/0035243 A1 | 2/2008 | Breitenkamp et al. | |
| 2008/0038472 A1 | 2/2008 | Suzuki et al. | |
| 2008/0045686 A1 | 2/2008 | Meagher et al. | |
| 2008/0050731 A1 | 2/2008 | Agnew et al. | |
| 2008/0051562 A1 | 2/2008 | Chaikof et al. | |
| 2008/0103564 A1 | 5/2008 | Burkinshaw et al. | |
| 2008/0121657 A1 | 5/2008 | Voegele et al. | |
| 2008/0138317 A1 | 6/2008 | Fung | |
| 2008/0160017 A1 | 7/2008 | Baker et al. | |
| 2008/0166363 A1 | 7/2008 | Govindan et al. | |
| 2008/0171067 A1 | 7/2008 | Govindan et al. | |
| 2008/0187956 A1 | 8/2008 | Carrico et al. | |
| 2008/0199736 A1 | 8/2008 | Gadeken et al. | |
| 2008/0200628 A1 | 8/2008 | Gadeken et al. | |
| 2008/0207913 A1 | 8/2008 | Breitenkamp et al. | |
| 2008/0214436 A1 | 9/2008 | Yu et al. | |
| 2008/0214801 A1 | 9/2008 | Saxon et al. | |
| 2008/0214831 A1 | 9/2008 | Sharpless et al. | |
| 2008/0221043 A1 | 9/2008 | Harth et al. | |
| 2008/0241856 A1 | 10/2008 | Wong et al. | |
| 2008/0241892 A1 | 10/2008 | Roitman et al. | |
| 2008/0242171 A1 | 10/2008 | Huang et al. | |
| 2008/0248126 A1 | 10/2008 | Cheng et al. | |
| 2008/0267878 A1 | 10/2008 | Robillard et al. | |
| 2008/0283572 A1 | 11/2008 | Boyden et al. | |
| 2008/0311412 A1 | 12/2008 | Fokin et al. | |
| 2008/0317861 A1 | 12/2008 | Guan | |
| 2009/0012457 A1 | 1/2009 | Childers et al. | |
| 2009/0018646 A1 | 1/2009 | Zhao | |
| 2009/0027603 A1 | 1/2009 | Samulski et al. | |
| 2009/0038701 A1 | 2/2009 | Delmotte | |
| 2009/0053139 A1 | 2/2009 | Shi et al. | |
| 2009/0054619 A1 | 2/2009 | Baker et al. | |

(56) References Cited

U.S. PATENT DOCUMENTS

| | | |
|---|---|---|
| 2009/0061010 A1 | 3/2009 | Zale et al. |
| 2009/0069561 A1 | 3/2009 | Fokin et al. |
| 2009/0082224 A1 | 3/2009 | Haddleton et al. |
| 2009/0099108 A1 | 4/2009 | Jones |
| 2009/0124534 A1 | 5/2009 | Reineke et al. |
| 2009/0137424 A1 | 5/2009 | Tsao et al. |
| 2009/0181402 A1 | 7/2009 | Finn et al. |
| 2009/0182151 A1 | 7/2009 | Wu et al. |
| 2009/0202433 A1 | 8/2009 | Chang et al. |
| 2009/0203131 A1 | 8/2009 | Reineke et al. |
| 2009/0214755 A1 | 8/2009 | Armani et al. |
| 2009/0220607 A1 | 9/2009 | Kiser et al. |
| 2009/0240030 A1 | 9/2009 | Ju et al. |
| 2009/0247651 A1 | 10/2009 | Kapiamba et al. |
| 2009/0250588 A1 | 10/2009 | Robeson et al. |
| 2009/0253609 A1 | 10/2009 | Fleury et al. |
| 2009/0259016 A1 | 10/2009 | Johnson et al. |
| 2009/0263468 A1 | 10/2009 | McAnulty et al. |
| 2009/0269277 A1 | 10/2009 | Chang et al. |
| 2009/0281250 A1 | 11/2009 | DeSimone et al. |
| 2009/0297609 A1 | 12/2009 | Shoichet et al. |
| 2009/0306310 A1 | 12/2009 | Wu et al. |
| 2009/0312363 A1 | 12/2009 | Bradner et al. |
| 2009/0325292 A1 | 12/2009 | Baker et al. |
| 2010/0011472 A1 | 1/2010 | Hugel et al. |
| 2010/0015046 A1 | 1/2010 | Govindan et al. |
| 2010/0021391 A1 | 1/2010 | Douglas et al. |
| 2010/0034862 A1 | 2/2010 | Laronde et al. |
| 2010/0047258 A1 | 2/2010 | Wang et al. |
| 2010/0048738 A1 | 2/2010 | Fleury et al. |
| 2010/0069578 A1 | 3/2010 | Faust et al. |
| 2010/0098640 A1 | 4/2010 | Cohen et al. |
| 2010/0104589 A1 | 4/2010 | Govindan et al. |
| 2010/0121022 A1 | 5/2010 | Musa et al. |
| 2010/0159508 A1 | 6/2010 | Yang et al. |
| 2010/0247433 A1 | 9/2010 | Tirrell et al. |
| 2010/0286405 A1 | 11/2010 | Fokin et al. |
| 2010/0291171 A1 | 11/2010 | Crescenzi et al. |
| 2010/0303754 A1 | 12/2010 | Turpin et al. |
| 2011/0008251 A1 | 1/2011 | Chang et al. |
| 2011/0052696 A1 | 3/2011 | Hult et al. |
| 2011/0060107 A1 | 3/2011 | Matyjaszewski et al. |
| 2011/0143435 A1 | 6/2011 | Stayton et al. |
| 2011/0177156 A1 | 7/2011 | Szoka, Jr. et al. |
| 2011/0183417 A1 | 7/2011 | Reineke |
| 2011/0213123 A1 | 9/2011 | Bertozzi et al. |

FOREIGN PATENT DOCUMENTS

| | | |
|---|---|---|
| EP | 0328050 A2 | 8/1989 |
| EP | 0490854 B1 | 9/1996 |
| EP | 1790702 A1 | 5/2007 |
| EP | 1795563 A1 | 6/2007 |
| EP | 2014308 A2 | 1/2009 |
| EP | 2090592 A1 | 8/2009 |
| WO | WO 99/11692 A1 | 3/1999 |
| WO | WO 99/28354 A1 | 6/1999 |
| WO | WO 00/62827 A2 | 10/2000 |
| WO | WO 01/68565 A2 | 9/2001 |
| WO | WO 03/101972 A1 | 12/2003 |
| WO | WO 2004/054622 A1 | 7/2004 |
| WO | WO 2005/062854 A2 | 7/2005 |
| WO | WO 2005/079217 A2 | 9/2005 |
| WO | WO 2005/084180 A2 | 9/2005 |
| WO | WO 2005/084367 A2 | 9/2005 |
| WO | WO 2005/087818 A1 | 9/2005 |
| WO | WO 2005/113605 A1 | 12/2005 |
| WO | WO 2006/005046 A2 | 1/2006 |
| WO | WO 2006/012569 A1 | 2/2006 |
| WO | WO 2006/050262 A2 | 5/2006 |
| WO | WO 2006/065266 A2 | 6/2006 |
| WO | WO 2006/084202 A2 | 8/2006 |
| WO | WO 2006/091894 A2 | 8/2006 |
| WO | WO 2006/107617 A2 | 10/2006 |
| WO | WO 2006/107786 A2 | 10/2006 |
| WO | WO 2006/107903 A2 | 10/2006 |
| WO | WO 2007/002109 A2 | 1/2007 |
| WO | WO 2007/003054 A1 | 1/2007 |
| WO | WO 2007/011696 A2 | 1/2007 |
| WO | WO 2007/011967 A2 | 1/2007 |
| WO | WO 2007/021762 A2 | 2/2007 |
| WO | WO 2007/021763 A2 | 2/2007 |
| WO | WO 2007/022070 A2 | 2/2007 |
| WO | WO 2007/027493 A2 | 3/2007 |
| WO | WO 2007/035296 A2 | 3/2007 |
| WO | WO 2007/039858 A2 | 4/2007 |
| WO | WO 2007/041394 A2 | 4/2007 |
| WO | WO 2007/041451 A2 | 4/2007 |
| WO | WO 2007/046893 A2 | 4/2007 |
| WO | WO 2007/047301 A2 | 4/2007 |
| WO | WO 2007/047609 A2 | 4/2007 |
| WO | WO 2007/047668 A2 | 4/2007 |
| WO | WO 2007/047796 A2 | 4/2007 |
| WO | WO 2007/056561 A2 | 5/2007 |
| WO | WO 2007/075270 A2 | 7/2007 |
| WO | WO 2007/081876 A2 | 7/2007 |
| WO | WO 2007/104948 A2 | 9/2007 |
| WO | WO 2007/112193 A2 | 10/2007 |
| WO | WO 2007/121055 A1 | 10/2007 |
| WO | WO 2007/125429 A2 | 11/2007 |
| WO | WO 2007/127473 A2 | 11/2007 |
| WO | WO 2007/132000 A1 | 11/2007 |
| WO | WO 2007/132005 A2 | 11/2007 |
| WO | WO 2008/004988 A1 | 1/2008 |
| WO | WO 2008/006097 A2 | 1/2008 |
| WO | WO 2008/008483 A2 | 1/2008 |
| WO | WO 2008/011335 A2 | 1/2008 |
| WO | WO 2008/013618 A1 | 1/2008 |
| WO | WO 2008/016371 A2 | 2/2008 |
| WO | WO 2008/017029 A2 | 2/2008 |
| WO | WO 2008/019450 A1 | 2/2008 |
| WO | WO 2008/024435 A2 | 2/2008 |
| WO | WO 2008/031525 A1 | 3/2008 |
| WO | WO 2008/036350 A2 | 3/2008 |
| WO | WO 2008/047057 A1 | 4/2008 |
| WO | WO 2008/048288 A2 | 4/2008 |
| WO | WO 2008/048733 A1 | 4/2008 |
| WO | WO 2008/060333 A1 | 5/2008 |
| WO | WO 2008/075955 A2 | 6/2008 |
| WO | WO 2008/077406 A2 | 7/2008 |
| WO | WO 2008/088658 A2 | 7/2008 |
| WO | WO 2008/091349 A1 | 7/2008 |
| WO | WO 2008/094254 A2 | 8/2008 |
| WO | WO 2008/101024 A2 | 8/2008 |
| WO | WO 2008/101069 A1 | 8/2008 |
| WO | WO 2008/105773 A2 | 9/2008 |
| WO | WO 2008/105902 A2 | 9/2008 |
| WO | WO 2008/106657 A2 | 9/2008 |
| WO | WO 2008/108736 A1 | 9/2008 |
| WO | WO 2008/115694 A2 | 9/2008 |
| WO | WO 2008/120016 A1 | 10/2008 |
| WO | WO 2008/121375 A2 | 10/2008 |
| WO | WO 2009/029242 A1 | 3/2009 |
| WO | WO 2009/064696 A1 | 5/2009 |
| WO | WO 2009/136853 A1 | 11/2009 |
| WO | WO 2009/140429 A2 | 11/2009 |
| WO | WO 2010/095049 A1 | 8/2010 |

OTHER PUBLICATIONS

Jérôme, et al., "Recent Advances in the Synthesis of Aliphatic Polyesters Ring-Opening Polymerization", Advanced Drug Delivery Reviews, 60, (2008), pp. 1056-1076.
Zhang, et al., "2-Azido-2-deoxycellulose: Synthesis and 1, 3-Dipolar Cycloaddition", Helvetica Chimica Acta, vol. 91, pp. 608-617 (2008) ; (Abstract Only).
R. Riva, et al., "Contribution of "Click Chemistry" to the Synthesis of Antimicrobial Aliphatic Copolyester", Polymer 49, (2008), pp. 2023-2028.
Baskin, et al., "Copper Free Click Chemistry for Dynamic In Vivo Imaging", PNAS, vol. 104, No. 43, (Oct. 23, 2007), pp. 16793-16797.
Codelli, et al., "Second Generation Difluorinated Cyclooctynes for Copper-Free Click Chemistry", J. Am. Chem. Soc., vol. 130, No. 34, (2008), pp. 11486-11493.

(56) References Cited

OTHER PUBLICATIONS

Sletten and Bertozzi, "A Hydrophilic Azacyclooctyne for Cu-free Click Chemistry", Org. Lett. (2008) 10(14), pp. 3097-3099.

Cazalis, et al., "C-Terminal Site-Specific PEGylatin of a Truncated Thrombomodulin Mutant with Retention of Full Bioactivity", Bioconjugate Chem., (2004), 15, pp. 1005-1009.

Haridas, et al., "Design and Synthesis of Triazole-based Peptidedendrimers" Tetrahedron Letters, vol. 48, (2007), pp. 4719-4722.

Raghavan, et al., "Chemical Probes for Profiling Fatty Acid-associated Proteins in Living Cells", Bioorg. Med. Chem. Lett., 18 (2008), pp. 5982-5986.

Le Dévédec, et al., "Separation of Chitosan Oligomers by Immobilized Metal Affinity Chromatography", Journal of Chromatography A., 2008, 1194(2), pp. 165-171.

Hartgerink, et al., "Peptide-amphiphile Nanofibers: A Versatile Scaffold for the Preparation of Self Assembling Materials", PNAS, 2002; 99(2), pp. 5133-5138.

Van Berkel, et al., "Metal-Free Triazole Formation as a Tool for Bioconjugation", Chem Bio Chem, 8, (2007), pp. 1504-1508.

Nottelet, et al., Synthesis of an X-ray opaque biodegradable copolyester by chemical modification of poly (ϵ-caprolactone) Biomaterials, 27, (2006), pp. 4943-4954.

Smith, et al., "Synthesis and Convenient Functionalization of Azide-labeled Diacyglycerol Analoges for Modular Access to Biologically Active Lipid Probes", Bioconjugate Chem, 19(9), (2008), pp. 1855-1863; (Abstract Only).

Skierka, et al., "The Influence of Different Acids and Pepsin on the Extractability of Collagen From the Skin of Baltic Cod (*Gadus morhua*)", Food Chemistry, 105, (2007), pp. 1302-1306.

Eastoe, "The Amino Acid Composition of Mammalian Collagen and Gelatin", vol. 61, (1955), pp. 589-600.

Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.

Laughlin, et al., "In Vivo Imaging of Membrane-Associated Glycans in Developing Zebrafish", Science, 320, (2008), pp. 664-667.

Worch and Wittmann, "Unexpected Formation of Complex Bridged Tetrazoles via Intramolecular 1,3-dipolar Cycloaddition of 1,2-0-cyanoalkylidene Derivatives of 3-azido-3-deoxy-D-allose", Carbohydrate Research, 343, (2008), pp. 2118-2129.

Witczak et al., "A click Chemistry Approach to Glycomimetics: Michael addition of 2,3,4,6-tetra-*O*-acetyl-1-thio-β-D-glucopyranose to 4-deoxy-1,2-*O*-isopropylident-L-*glycero*-pent-4-enopyranose-3-ulose-a convenient route to novel 4-deoxy-(1→5)-5-*C*-thiodisaccharides", Carbohydrate Research, 342, (2007), 1929-1933.

Marra, et al., "Validation of the Copper(l)-Caralyzed Azide-Alkyne Coupling in Ionic Liquids, Synthesis of a Triazole-Linked C-Disaccharide as a Case Study", J. Org. Chem (2008), 73(6), pp. 2458-2461; (Abstract Only).

Srinivasachari, et al., "Versatile Supramolecular pDNA Vehicles via "Click Polymerization" of β-cyclodextrin with oligoethyleneamines", Biomaterials, 30, (2009), pp. 928-938.

Arora, et al., "A Novel domino-click approach for the synthesis of sugar based unsymmetrical bis-1,2,3-triazoles", Carbohydrate Research, 343, (2008), 139-144.

Chen, et al., "Synthesis of a $C_3$-symmetric (1→6)-*N*-acetyl-β-D-glucosamine Octadecasaccharide using Click Chemistry", Carbohydrate Research, 340, (2005), pp. 2476-2482.

Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045; (Abstract Only).

Srinivasachari, etal., "Effect of Trehalose Click Polymer Length on pDNA Complex Stability and Delivery Efficacy", Biomaterials, 28, (2007), pp. 2885-2898.

Godeau, et al., Lipid-Conjugated Oligonucleotides via "Click Chemistry" Efficiently Inhibit Hepatitis C Virus Translation, J. med. Chem., 2008, 51(15), pp. 2374-4376; (Abstract Only).

Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.

Cantel, et al., "Synthesis and Conformational Analysis of a Cyclic Peptide Obtained via *i* to *i* + 4 Intramolecular Side-chain to Side-chain Azide-Alkyne 1,3-Dipolar Cycloaddition", J. Org. Chem., 2008, 73 (15), pp. 5663-5614; (Abstract Only).

Dijk, et al., Synthesis of Peptide-Based Polymers by Microwave-Assisted Cycloaddition Backbone Polymerization, Biomacro molecules, 2007, 8(2), pp. 327-330; (Abstract Only).

Köster, et al., "Spectroscopic and Electrochemical Studies of Ferroceryl Triazole Amino Acid and Peptide Bioconjugates Synthesized by Click Chemistry", Organometallics, 2008, 27(23) pp. 6326-6332; (Abstract Only).

Dijk, et al., "Synthesis and Characterization of Biodegradable Peptide-Baed Polymers Prepared by Microwave-Assisted Click Chemistry", Biomacromolecules; 2008, 9(10), pp. 2834-2843; (Abstract Only).

Jiang, et al., "Amphiphilic PEG/alkyl-grafted comb polyactides", J. Polymer Science Part B: Polymer Physics, 45(22), 2007, pp. 5227-5236; (Abstract Only).

Ochs, et al., "Low-Fouling, Biofunctionalized, and Biodegradable Click Capsules", Biomacromolecules, 2008, 9(12), pp. 3389-3396; (Abstract Only).

Beatty and Tirrell, "Two-color Labeling of Temporally Defined Protein Populations in Mammalian Cells", Bioorg. Med. Chem. Lett., 18 (2008), pp. 5995-5999.

Kolb, et al., "Click Chemistry: Diverse Chemical Function from a Few Good Reactions", Angewandte Chemie, International Edition, Jun. 2001, pp. 2004-2021.

Krouit, et al., "Cellulose surface grafting with polycaprolactone by heterogeneous click-chemistry", European Polymer Journal 44, Dec. 2008, pp. 4074-4081; (Abstract Only).

Nandivada, et al. "Reactive polymer coatings that 'Click'", Angewandte Chemie, International Edition 45, Apr. 2006, pp. 3360-3363; (Abstract Only).

Ossipov and Hilborn, Poly(vinyl alcohol)-Based Hydrogels Formed by "Click Chemistry", Macromelecules 2006, 39, pp. 1709-1718.

Binder and Sachsenhofer, "Click Chemistry in Polymer and Materials Science", Macromolecular Rapid Commun. 2007, 28, pp. 15-54.

European Search Report, Application No. 11804173 dated May 12, 2015.

International Search Report corresponding to PCT/US11/042336 mailed Nov. 3, 2011.

\* cited by examiner

MICROWAVE-POWERED REACTOR AND METHOD FOR IN SITU FORMING IMPLANTS

BACKGROUND

1. Technical Field

The present disclosure relates to crosslinked polymers, and more particularly to the use of click chemistry and microwave technology to form the crosslinked polymers, methods of preparing such polymers, and medical devices made from such polymers.

2. Background of Related Art

Click chemistry refers to a collection of reactions capable of forming a highly reliable molecular connection in solution or bulk state. Click chemistry reactions may be highly selective, high yield reactions which should not interfere with one another as well as other reactions.

Microwave energy may be utilized to assist chemical reactions. Microwave powered reactions may be fast and result in a higher and/or purer yield. Thus, it would be desirable to make an injectable medical device by mixing and dispensing first and second precursors functionalized for crosslinking by click chemistry using microwave technology for placement in situ.

SUMMARY

The present disclosure relates to devices and processes for forming medical devices from one or more injectable compositions. An apparatus in accordance with the present disclosure includes a supply assembly, a mixing assembly, and at least one source of microwave energy. The supply assembly is configured to maintain and selectively dispense a first precursor functionalized with a first reactive member and a second precursor functionalized with a second reactive member. The mixing assembly is configured to mix the first and second precursors within a mixing cavity defined therein. The microwave energy source is configured and adapted to irradiate the mixed first and second precursors within the mixing cavity.

In embodiments, the source of microwave energy includes a microwave generator operably coupled to a microwave antenna. The microwave antenna includes a radiating section that is disposed within the mixing cavity. In embodiments, the source of microwave energy includes a microwave generator operably coupled to the mixing cavity. The mixing cavity is configured as a substantially closed reactor for receiving microwave energy from the microwave generator.

The mixing cavity may include a mixing element to aid in the homogeneous mixing and crosslinking of the first and second precursors. In embodiments, the mixing element is a static mixer including substantially fixed helical members extending along a length of the mixing cavity.

A catalyst, such as a transition metal ion, may be incorporated into the mixing cavity of the present apparatus to further aid in the polymerization of the first and second precursors. In embodiments, at least a portion of the mixing cavity includes a coating containing a catalyst. In embodiments utilizing a mixing element, at least a portion of the mixing element and/or mixing cavity may include a coating containing a catalyst.

A process of forming an injectable medical device according to the present disclosure includes dispensing a volume of a first precursor functionalized with a first reactive member and a volume of a second precursor functionalized with a second reactive member into a mixing assembly, mixing the first and second precursors, and exposing the mixed first and second precursors to microwave energy to produce a flowable composition for use as a medical device.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

DETAILED DESCRIPTION OF THE EMBODIMENTS

Figure 1:
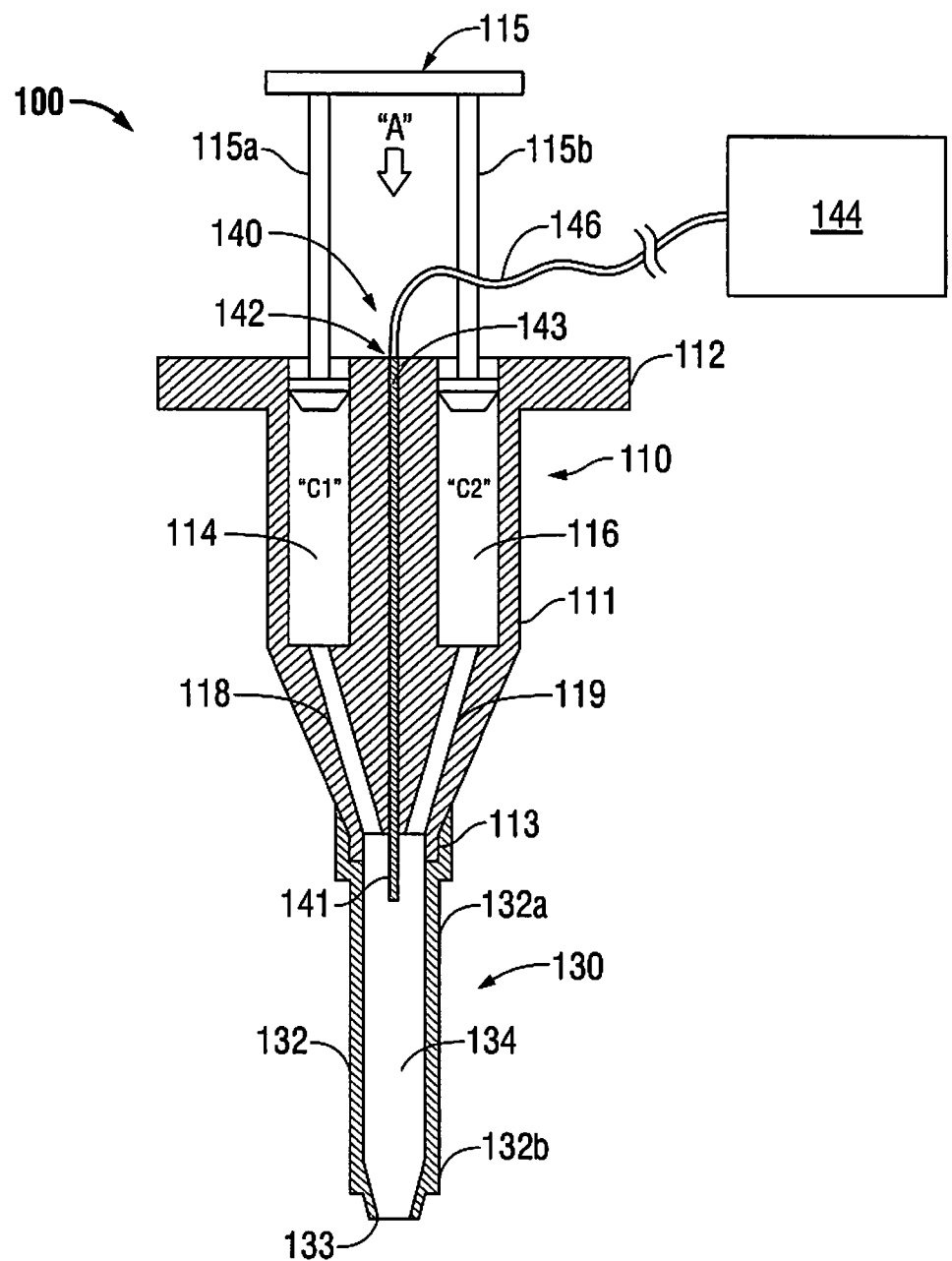
FIG. 1 is a cross-sectional view of an apparatus for mixing and catalyzing first and second precursors to form medical devices in accordance with the present disclosure.

Cross-linked compositions in accordance with the present disclosure include a first precursor functionalized with a first reactive member and a second precursor functionalized with a second reactive member. The first and second reactive members covalently bond with each other when exposed to microwave energy. The compositions are useful in a variety of surgical and wound treatment applications.

The first and second precursors may each possess a core functionalized with a reactive member. Suitable components for use as the core(s) include, but are not limited to, monomers, oligomers, macromers, polymers, and the like. The reactive member(s) may be, for example, an amine, sulfate, thiol, hydroxyl, azide, alkyne, alkene, and carboxyl group.

The core of the first and second precursors may be any suitable biocompatible material. In embodiments, the first and second precursors may be different biocompatible materials, thus forming copolymer cross-linked compositions. The cross-linked compositions may be formed from a natural material or a synthetic material which may be bioabsorbable or non-bioabsorbable. It should of course be understood that any combination of natural, synthetic, bioabsorbable, and non-bioabsorbable materials may be used to form the cross-linked compositions. Thus, the core may be linear, branched, star-shaped, dendrimeric, and the like.

In embodiments, suitable cores for use as the first and second precursors may be prepared from a polyol, a polyamine, or a polythiol. In embodiments a polyol may be used to form a core. Examples of such polyols include, in embodiments, polyethers, polyesters, polyether-esters, polyalkanols, combinations thereof, and the like.

Suitable polyethers which may be utilized in forming the core of the first precursor and/or the second precursor are within the purview of those skilled in the art and include, for example, poly(alkylene glycols), such as poly(ethylene glycol), poly(propylene glycol), poly(butylene glycol), poly(tetramethylene glycol), poly(hexamethylene glycol), copolymers such as cyclodextrin-poly(alkylene glycols), polyacetals, and combinations thereof. In embodiments a suitable polyether may include poly(ethylene glycol).

Suitable polyesters which may be utilized in forming the core of the first precursor and/or the second precursor are within the purview of those skilled in the art and include, for example, poly(trimethylene carbonate), poly(ε-caprolactone), poly(p-dioxanone), poly(glycolide), poly(lactide), poly(1,5-dioxepan-2-one), poly(butylene adipate), poly(ethylene adipate), poly(ethylene terephthalate), dipoly(ethylene glycol) adipate, and combinations thereof.

In addition, as noted above, the first precursor and/or the second precursor may include a poly(ether-ester) block. Any suitable poly(ether-ester) block within the purview of those skilled in the art may be utilized. These macromers may include an aliphatic diacid, aromatic diacid, alicyclic diacid, or combinations thereof, linking two dihydroxy compounds (sometimes referred to herein as a "poly(ether-ester) macromer"). Up to ten repeats of the poly(ether-ester) macromer may be present.

Suitable diacids which may be utilized in forming the poly(ether-ester) macromer include, for example, diacids having from about 2 to about 10 carbon atoms. Suitable diacids include, but are not limited to, sebacic acid, azelaic acid, suberic acid, pimelic acid, adipic acid, glutaric acid, succinic acid, malonic acid, oxalic acid, terephthalic acid, cyclohexane dicarboxylic acid, and combinations thereof.

Suitable dihydroxy compounds which may be utilized in forming the poly(ether-ester) macromer include, for example, polyols including polyalkylene oxides, polyvinyl alcohols, polycaprolactone diols, and the like. In some embodiments, the dihydroxy compounds can be a polyalkylene oxide such as polyethylene oxide ("PEO"), polypropylene oxide ("PPO"), block or random copolymers of polyethylene oxide (PEO) and polypropylene oxide (PPO), and combinations thereof.

In one embodiment, a polyethylene glycol ("PEG") may be utilized as the dihydroxy compound. It may be desirable to utilize a PEG with a molecular weight of from about 200 g/mol to about 10000 g/mol, in embodiments from about 400 g/mol to about 900 g/mol. Suitable PEGs include those commercially available from a variety of sources under the designations PEG 200, PEG 400, PEG 600, and PEG 900.

Any method may be used to form the poly(ether-ester) macromer. In some embodiments, the poly(ether-ester) macromer may be formed by combining adipoyl chloride with a PEG such as PEG 600 and pyridine in a suitable solvent, such as tetrahydrofuran (THF). The solution may be held at a suitable temperature, from about −70° C. to about +25° C., for a period of time of from about 4 hours to about 18 hours, after which the reaction mixture may be filtered to remove the precipitated pyridine hydrochloride by-product and the resulting poly(ether-ester) macromer, here a PEG/adipate compound. The resulting poly(ether-ester) macromer may be obtained from the solution by the addition of an ether or petroleum ether, and collected by suitable means which can include filtration. Other methods suitable for producing such macromers are within the purview of those skilled in the art.

In embodiments, components utilized in forming poly(ether-esters) may be functionalized and reacted to form poly(ether-ester-urethanes), poly(ether-ester-ureas), and the like.

Other examples of suitable poly(ether-ester) blocks which may be utilized include, but are not limited to, polyethylene glycol-polycaprolactone, polyethylene glycol-polylactide, polyethylene glycol-polyglycolide, and various combinations of the individual polyethers and polyesters described herein. Additional examples of suitable poly(ether-ester) blocks include those disclosed in U.S. Pat. No. 5,578,662 and U.S. Patent Application No. 2003/0135238, the entire disclosures of each of which are incorporated by reference herein.

In embodiments, the resulting poly(ether-ester) macromer may be of the following formula:

$$\text{HO}—(X-A)_y-X—\text{OH} \quad (I)$$

wherein A is a group derived from an aliphatic, aromatic, or alicyclic diacid; X can be the same or different at each occurrence and may include a group derived from a dihydroxy compound; and y may be from about 1 to about 10. In some embodiments, the A group can be derived from adipic acid, and X can be derived from a polyethylene glycol having a molecular weight of from about 200 g/mol to about 1000 g/mol, in embodiments from about 400 g/mol to about 800 g/mol, in embodiments about 600 g/mol.

The molecular weight and viscosity of these compounds may depend on a number of factors such as the particular diacid used, the particular dihydroxy compound used, and the number of repeat units present. Generally, the viscosity of these compounds may be from about 300 cP to about 10,000 cP at 25° C. and a shear rate of 20.25 sec$^{-1}$.

In other embodiments, polyrotaxanes may be utilized as the core of the first precursor and/or the second precursor. Polyrotaxane materials include cyclic molecules, linear molecules threaded through the cyclic molecules, and optionally bulky end groups on the linear molecules to prevent the loss of the cyclic molecules by dethreading. With respect to rotaxanes, "linear molecules" refers to any suitable molecules, whether branched or unbranched, that are capable of threading the cyclic molecules to form the rotaxane material. The linear molecules are generally in the form of chains that are unbranched. Branching of the linear molecules may occur, but not to the extent that the branching significantly interferes with the formation of the rotaxane material.

Examples of suitable polyrotaxanes include those created by linear polymers such as poly(ethylene oxide) (PEO) penetrating the inner cavity of cyclodextrins (CDs) to form inclusion complexes with a necklace-like supramolecular structure.

In embodiments, the polyol, such as a polyether, polyester, or polyether-ester as described above, may be a branched polyol. Such a polyol may have a central core from which from about 3 to about 12 arms may extend, with hydroxyl groups at the free terminal of each arm. In embodiments, for example, a 4-armed polyol may have the following structure:

(II)

In embodiments, the polyol, such as a polyether, polyester, or polyether-ester as described above, may be endcapped with functional groups. In embodiments, where one of the precursors is endcapped with two groups, the other precursor may be endcapped with three or more groups. Methods for endcapping the polyol to provide a reactive end group are within the purview of those skilled in the art.

The first precursor and the second precursor each have at least one reactive member known to have click reactivity when exposed to microwave energy. In embodiments, the precursors may have from about 2 to about 50 reactive members. The click chemistry reaction of the present disclosure includes first and second precursors each having terminal and/or side chain functionality. The first and second precursors are functionalized by converting an attached functional unit on the precursor thereby providing site specific functional materials, site specific functional materials comprising additional functionality, or chain extended functional materials. Optionally, a linker may or may not be present for linking a functional group to the precursor. These reactive members may form arms extending from the core(s).

In embodiments, for example, the 4-armed polyol of formula II may be functionalized to include an alkyne of the following formula:

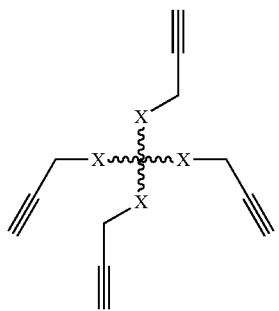

(III)

wherein X may be O, NH, S, $SO_2$, combinations thereof, and the like.

Click chemistry refers to a collection of reactive members having a high chemical potential energy capable of producing highly selective, high yield reactions. The reactive members react to form chemical bonds that are extremely stable in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-dipolar compounds contain one or more heteroatoms and can be described as having at least one mesomeric structure that represents a charged dipole. They include nitril oxides, azides, and diazoalkanes.

In embodiments, a click chemistry reaction of a Huisgen 1,3-dipolar cycloaddition reaction between alkyl-aryl-sulfonyl azides, C—N triple bonds, and C—C triple bonds assisted by microwave irradiation is well-suited for use herein.

In embodiments, the first precursor possesses at least one azide group and the second precursor possesses at least one alkyne group. Reaction of alkynes and azides is very specific and essentially inert against the chemical environment of biological tissues. For example, the above alkyne of formula III may be reacted with a polyazide. Suitable azides include, for example, (IV)

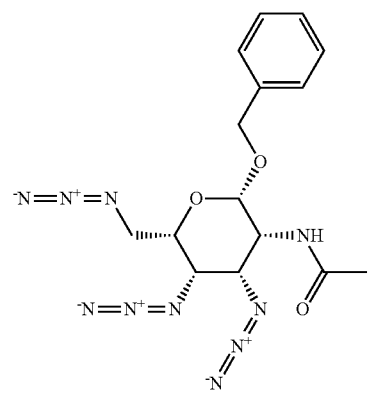

N-((2S,3R,4S,5S,6S)-4,5diazido-6-(azidomethyl)-2-(benzyloxy)tetrahydro-2H-pyran-3-yl)acetamide (V)

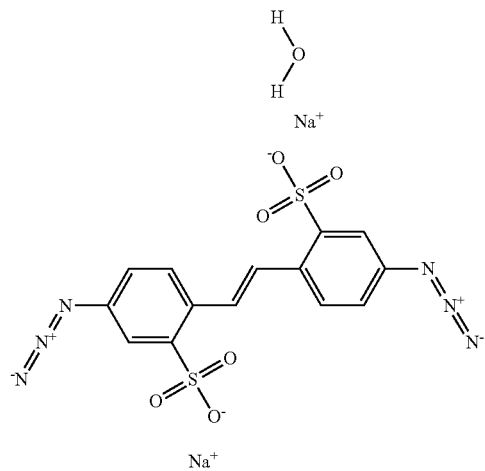

4,4'-Diazido-2-2'-stilbenedisulfonic acid disodium salt hydrate (VI)

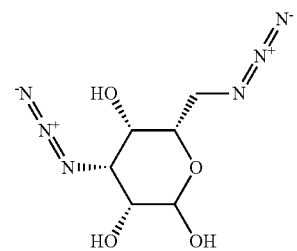

(3R,4R,5S,6S)-4-azido-6-(azidomethyl)tetrahydro-2H-pyran-2,3,5-triol

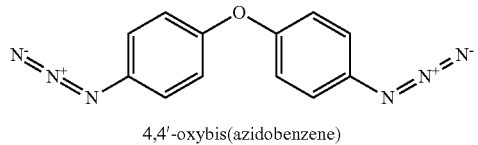

4,4'-oxybis(azidobenzene) (VII)

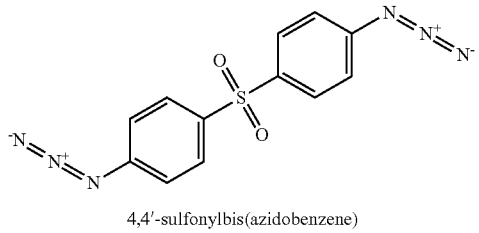

4,4'-sulfonylbis(azidobenzene) (VIII)

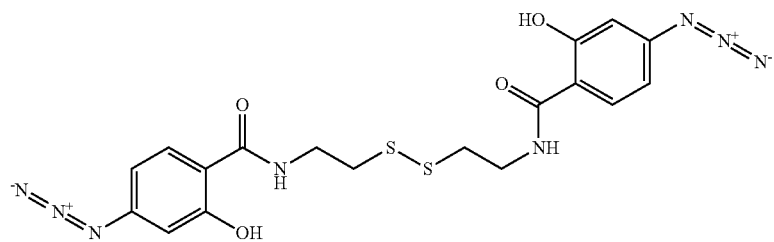

bis[2-(4-azidosalicylamido)ethyl]disulfide (IX)

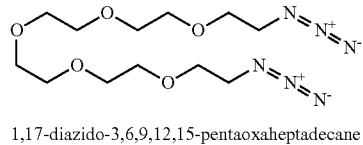

1,17-diazido-3,6,9,12,15-pentaoxaheptadecane (X)

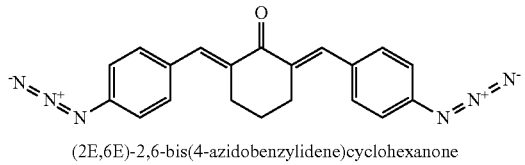

(2E,6E)-2,6-bis(4-azidobenzylidene)cyclohexanone (XI)

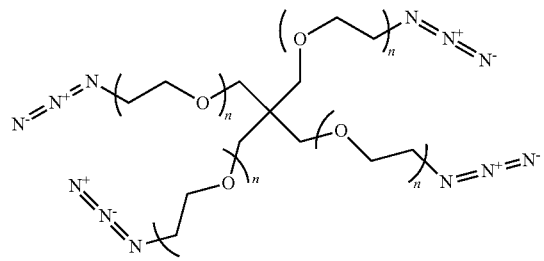

tetraazido-pentaerythritol ethoxylatedheptakis-6-azido-6-deoxy-beta-cyclodextrin (XII)

combinations thereof, and the like.

The alkyne of formula III may be reacted with an azide utilizing microwave energy to produce a compound of the present disclosure having the following structure:

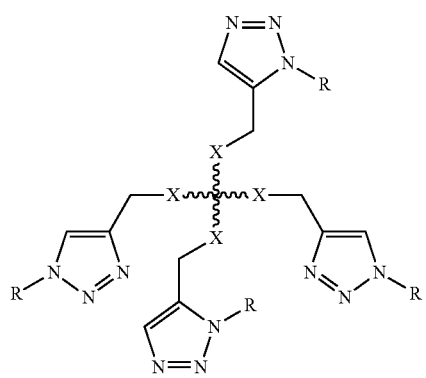

(XIII)

wherein X is as defined above for formula III and R may be the remainder of the polyazide component, i.e., a fragment of a polyazide molecule wherein the azide group is linked to the rest of the molecule through an alkyl group, alicyclic group, aromatic group, combinations thereof, and the like.

In other embodiments, a branched alkyne may be of the following formula

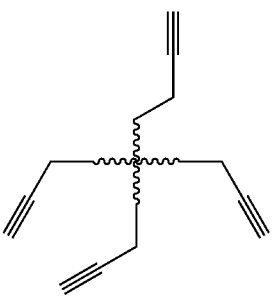

(XIV)

Other branched alkynes include, for example,
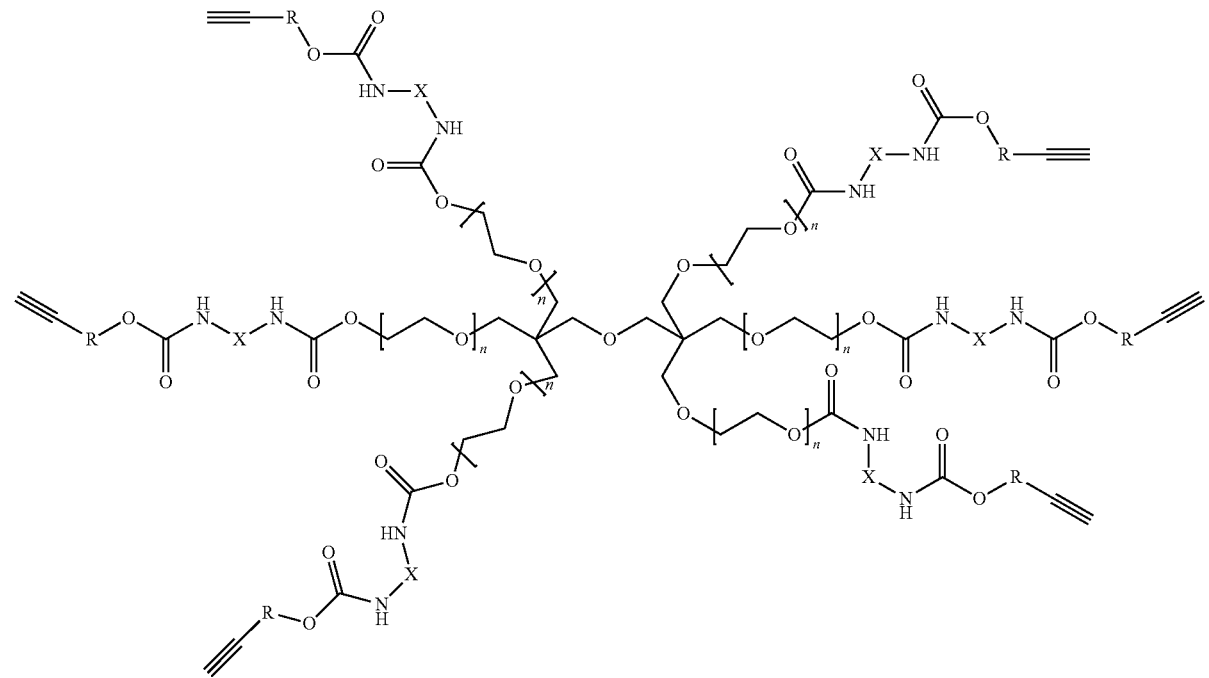
(XV)
wherein X may be aliphatic, alicyclic, aromatic, or a combination thereof, and
wherein R may be aliphatic, alicyclic, aromatic, or a combination thereof;
wherein Y may be aliphatic, alicyclic, aromatic, or a combination thereof, and
wherein R may be aliphatic, alicyclic, aromatic, or a combination thereof; and
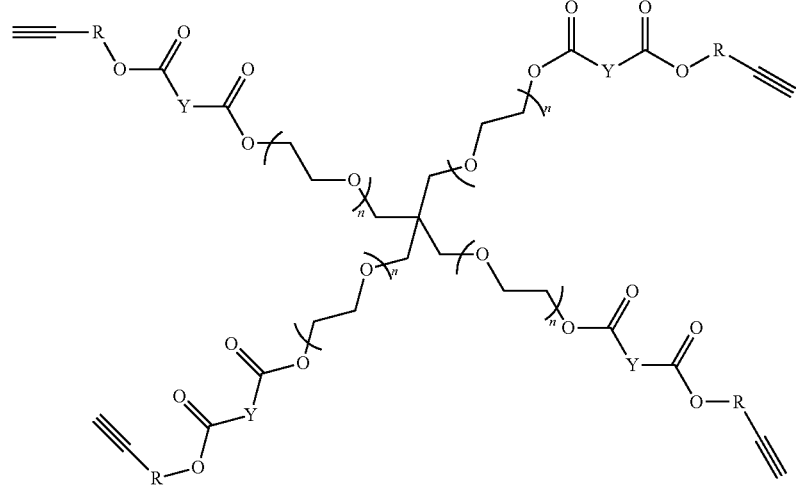
(XVI)

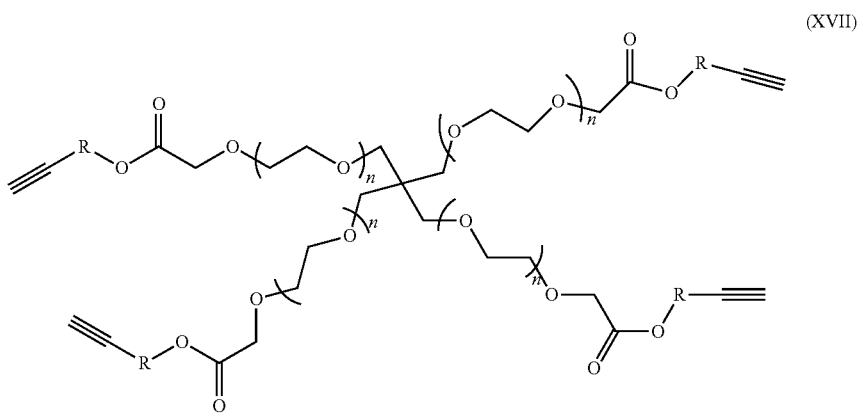

(XVII)

wherein R may be aliphatic, alicyclic, aromatic, or a combination thereof, and n in any of the formulas above may be a number from about 0 to about 112, in embodiments from about 1 to about 100, in other embodiments from about 3 to about 56.

A branched azide may have from about 3 to about 12 arms, in embodiments from about 4 to about 6 arms. An exemplary 4-armed branched azide may have the following generic formula

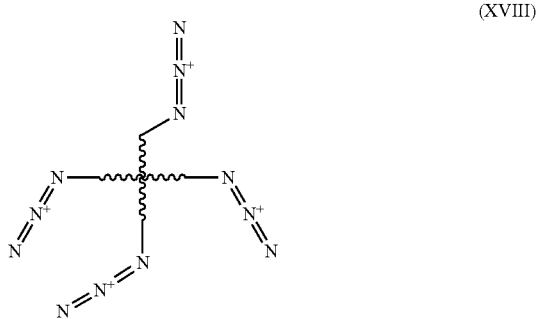

(XVIII)

The alkyne of formula V and the azide of formula VI may then be reacted and subject to microwave irradiation to produce the following compound:

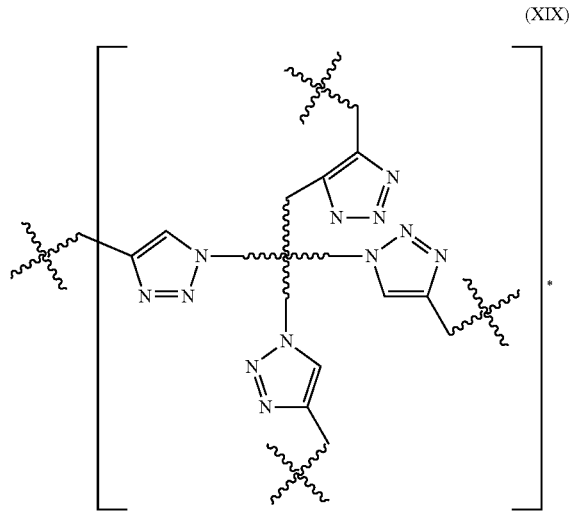

(XIX)

In preparing compositions in accordance with the present disclosure, the first and second precursors may be commercially available pre-functionalized cores or may be synthesized. For example, pendant chlorides on a core may be converted into azides by reaction with sodium azide. Those skilled in the art reading this disclosure will readily envision chemical reactions for activating other core materials to render them suitable for use as precursors in the presently described methods.

The first and second precursors may take the form of any solution, suspension, semi-solid, or solid material capable of allowing the two components to interact and crosslink. The first and second precursors may be in granular, pellet, or powder form, or alternatively, may be in solution. Suitable solvents which may be utilized to form a dilute solution include any biocompatible solvent within the purview of those skilled in the art which will not interfere with the reaction of the reactive members of the first and second precursors. Suitable solvents which may be utilized include, for example, polar solvents such as water, ethanol, triethylene glycol, dimethyl sulfoxide, glymes (such as diglyme, triglyme, tetraglyme, and the like), poly(ethylene glycols), methoxy-poly(ethylene glycols), dimethylformamide, dimethylacetamide, gamma-butyrolactone, n-methylpyrollidone, ketones such as methyl ethyl ketone, cyclohexanone, diethylene glycol momethyl ether acetate, diethylene glycol monobutyl ether acetate, diethylene glycol monomethyl ether, diethylene glycol monoethyl ether, diethylene glycol monobutyl ether, diethylene glycol monoisobutyl ether, diisobutyl ketone, diacetone alcohol, ethyl amyl ketone, ethyl lactate, and the like. In other embodiments, solvents such as tetrahydrofuran, ethyl acetate, isopropyl acetate, butyl acetate, isopropanol, butanol, acetone, and the like, may be utilized. In embodiments, combinations of any of the foregoing solvents may be utilized to form a dilute solution. The amount of solvent used will depend on a number of factors, including the particular first precursor, second precursor, or combination thereof that are to be employed and the intended end use of the composition.

The rate of cross-linking of the first and second precursors of the present disclosure may be tailored by controlling the concentration of the first precursor and the second precursor. Generally, a faster cross-linking time may be observed at a higher concentration of either the first or second precursors than the rate observed for the same components at a lower concentration. In embodiments, the ratio of first precursor reactive members to second precursor reactive members is from about 1:2 to about 1:1. Alternatively, the rate of cross-linking may be adjusted by varying the microwave frequency or time of exposure.

Initiation of polymerization is accomplished by irradiation with microwaves which is a form of electromagnetic energy with frequencies between about 300 MHz to about 300 GHz. The microwaves directly couple with the molecules present in the reaction mixture thus leading to a fast rise in temperature and a faster reaction time.

The injectable composition may optionally be formulated to achieve delivery of a bioactive agent. Thus, in some embodiments, at least one bioactive agent may be combined with either the first precursor or the second precursor, introduced separately through the fluid applicator device, and/or may be separately applied to finished medical device. The agents may be freely admixed with the precursors (making sure not reactive with them) or may be tethered to the precursors through any variety of chemical bonds. In these embodiments, the present injectable composition can also serve as a vehicle for delivery of the bioactive agent.

The term "bioactive agent," as used herein, is used in its broadest sense and includes any substance or mixture of substances that have clinical use. Consequently, bioactive agents may or may not have pharmacological activity per se, e.g., a dye or a fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, and enzymes. It is also intended that combinations of bioactive agents may be used.

Anti-adhesive agents can be used to prevent adhesions from forming between the implantable medical device and the surrounding tissues opposite the target tissue. In addition, anti-adhesive agents may be used to prevent adhesions from forming between the coated implantable medical device and the packaging material. Some examples of these agents include, but are not limited to hydrophilic polymers such as poly(vinyl pyrrolidone), carboxymethyl cellulose, alginates, hyaluronic acid, poly(ethylene oxide), poly(vinyl alcohols), and combinations thereof.

Suitable antimicrobial agents which may be included as a bioactive agent include triclosan, also known as 2,4,4'-trichloro-2'-hydroxydiphenyl ether; chlorhexidine and its salts, including chlorhexidine acetate, chlorhexidine gluconate, chlorhexidine hydrochloride, and chlorhexidine sulfate; silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin; tetracycline; aminoglycosides such as tobramycin and gentamicin; rifampicin; bacitracin; neomycin; chloramphenicol; miconazole; quinolones such as oxolinic acid, norfloxacin, nalidixic acid, pefloxacin, enoxacin and ciprofloxacin; penicillins such as oxacillin and pipracil; nonoxynol 9; fusidic acid; cephalosporins; and combinations thereof. In addition, antimicrobial proteins and peptides such as bovine lactoferrin and lactoferricin B may be included as a bioactive agent in the present disclosure.

Other bioactive agents include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; antiparkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics; estrogens; antibacterials; antibiotics; anti-fungals; anti-virals; anticoagulants; anticonvulsants; antidepressants; antihistamines; and immunological agents.

Other examples of suitable bioactive agents, which may be included in the medical device of the present disclosure include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons ($\beta$-IFN, $\alpha$-IFN and $\gamma$-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids such as antisense molecules, DNA, RNA, RNAi; oligonucleotides; polynucleotides; and ribozymes.

With reference now to the figures, embodiments of an apparatus for mixing and catalyzing a mixture composed of two or more components or precursors will be described. Like reference numerals will refer to similar structure throughout the embodiments. As shown in the drawings and described throughout the following description, and as is traditional, the term "proximal" refers to the portion of the apparatus which is closer to the user and the term "distal" refers to the portion of the apparatus which is further away from the user.

Referring initially to FIG. 1, an apparatus according to an embodiment of the present disclosure is shown generally as fluid applicator 100. Applicator 100 includes a supply assembly 110 and a mixing assembly 130 operably connected to supply assembly 110. Supply assembly 110 is configured to maintain and selectively dispense a first and second component to mixing assembly 130. Mixing assembly 110 is configured to mix the first and second components and catalyze the resulting mixture.

Still referring to FIG. 1, as shown, supply assembly 110 includes a housing 111 configured for operable hand-held engagement by a user. Housing 111 includes a flange member 112 formed on a proximal end for facilitating engagement by a user and an extension 113 formed on a distal end for selectively positioning mixing assembly 130 relative to a target site. In one embodiment, extension 113 is of a sufficient length to position a distal end of mixing assembly 130 within the body cavity of a patient while maintaining supply assembly 110 outside of the body. In this manner, extension 113 may include a wire or other element (not shown) for maintaining extension 113 in a flexed or bent condition. Housing 111 further includes first and second component chambers 114, 116 configured to receive a first and second component "C1", "C2", respectively. A plunger assembly 115, including first and second plunger members 115a, 115b, operably engages housing 111 and is configured for selectively dispensing first and second components "C1", "C2" from first and second chambers 114, 116, respectively, in a syringe-like manner.

Housing 111 further includes first and second component conduits 118, 119 that fluidly communicate first and second chambers 114, 116, respectively, with mixing assembly 130. First and second component conduits 118, 119 extend distally from first and second chambers 114, 116, respectively, through extension 113 of housing 111. In an alternative embodiment, first and second component conduits 118, 119 may form a single conduit to permit mixing of first and second components "C1", "C2" prior to reaching mixing assembly 130.

Although shown as a hand-held apparatus capable of dispensing only two components, it is envisioned that the aspects of the present disclosure may be adapted for use with any known supply assembly capable of selectively dispensing two or more components. Alternative supply assemblies may be configured to dispense more than two components, remotely dispense the components, e.g., from a cart mounted supply assembly via a conduit or other tubing, and/or dispense the components at different rates to produce mixtures composed of different percentages of the components.

Mixing assembly 130 includes a substantially elongate member 132 including an open proximal end 132a, a substantially closed distal end 132b, and defining a mixing cavity 134 therebetween. Proximal end 132a of elongate member 132 is configured for operable engagement with extension 113 of housing 111. Proximal end 132a may be configured for frictional engagement with extension 113, as shown, or may instead be configured for mechanical fastening to extension 113, such as with a bayonet coupling, snap-fit fitting, threading, and the like. Mixing assembly 130 engages extension 113 such that mixing cavity 134 is maintained in fluid communication with first and second chambers 114, 116 of housing 111 via first and second conduits 118, 119. Distal end 132b of mixing assembly 130 defines an opening or outlet 133 configured for dispensing the mixture of first and second components "C1", "C2" from mixing cavity 134. Depending on the mixture and/or the desired method of application, outlet 133 may include a single bore, as shown, or may instead include multiple openings, a spray tip, a needle tip and/or any other suitable configuration.

Applicator 100 further includes a microwave power assembly 140 that includes a microwave antenna 142 coupled to a microwave generator 144. Examples of suitable microwave power assemblies which may be utilized with the present disclosure include penetrating microwave energy delivery devices sold by Covidien under the trademark Evident™.

As shown in FIG. 1, the microwave antenna 142 is operably connected to the microwave generator 144 via a flexible coaxial cable 146, however, it is also envisioned that the microwave generator 144 may be integrally formed with applicator 100 or be remotely connected to the microwave antenna 142. For example, microwave generator 144 may include a transmitter for wireless communication with a receiver in the wireless antenna 142. Microwave generator 144 may be manually activated, or alternatively, applicator 100 may include a sensor or other suitable device (not shown) for activating microwave generator 144 upon depression of plunger assembly 115.

Microwave antenna 142 includes a radiating section 141 disposed within the mixing cavity 134 and is connected by feedline 143 to the cable 146. In embodiments, the microwave generator is configured to provide microwave energy at an operational frequency from about 300 MHz to about 20,000 MHz, in embodiments, from about 500 MHz to about 10,000 MHz.

To operate applicator 100, first and second components "C1", "C2" are initially received within first and second component chambers 114, 116, respectively, and plunger assembly 115 is operably engaged with housing 111. Prior to or following the addition of first and second components "C1", "C2" to housing 111, mixing assembly 130 is operably connected to extension 113 of housing 111. In this manner, applicator 100 is ready for use.

By depressing plunger assembly 115, in the direction of arrow "A", first and second components "C1", "C2" are dispensed from first and second chambers 114, 116, respectively, through respective first and second conduits 118, 119. Initial mixing of first and second components "C1", "C2" occur as first and second components exit first and second conduits 118, 119. As initially mixed first and second components "C1", "C2" flow through mixing cavity 134, first and second components "C1", "C2" are exposed to the microwave energy generated by the microwave generator 144. In embodiments, the first and second components "C1", "C2" may be allowed to remain in the mixing cavity 134 for a predetermined period of time to allow for adequate exposure to the microwave energy. In embodiments, the first and second components "C1", "C2" are irradiated within the mixing cavity for about 1 minute to about 10 minutes. Continued depression of plunger assembly 115 causes the release of the resulting catalyzed mixture from outlet 133 of mixing assembly 130. As detailed above, outlet 133 may include various configurations, depending on the mixture being dispensed and the desired method of application.

Figure 2:
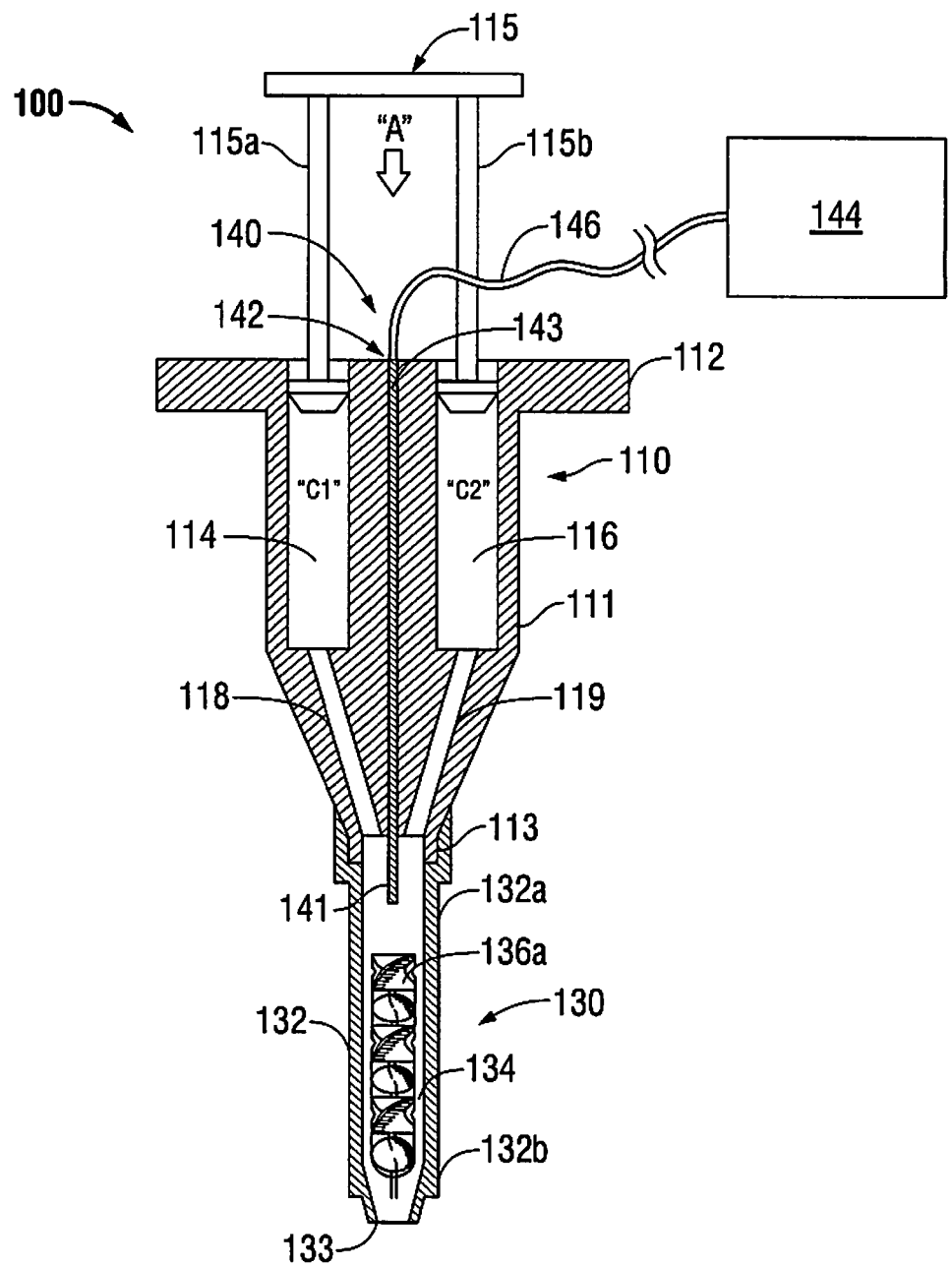
FIG. 2 is a cross-section view of the apparatus of FIG. 1 including mixing elements in accordance with an embodiment of the present disclosure.

To aid in homogeneous mixing and thorough exposure of the components to the microwave energy, the mixing assembly may include mixing elements. FIG. 2 illustrates a plurality of mixing elements 136a extending along at least a portion of the length of mixing cavity 134. Mixing elements 136a may form substantially fixed helical members, as shown, or may instead include multiple planar or curved blades, a single rotatable helical screw or any other suitable configuration for mixing first and second components "C1", "C2". The size, construction and spacing of mixing elements 136a may vary depending upon the composition of the components being mixed as well as the composition of the resulting mixture. As shown, mixing elements 136a are arranged in an alternating orientation to increase the turbulence of first and second components "C1", "C2" as the components flow through mixing cavity 134. The length of mixing assembly 130 and/or the rate through which the mixture flows therethrough may vary depending on the desired exposure time of the mixture to the microwave.

Figure 3A:
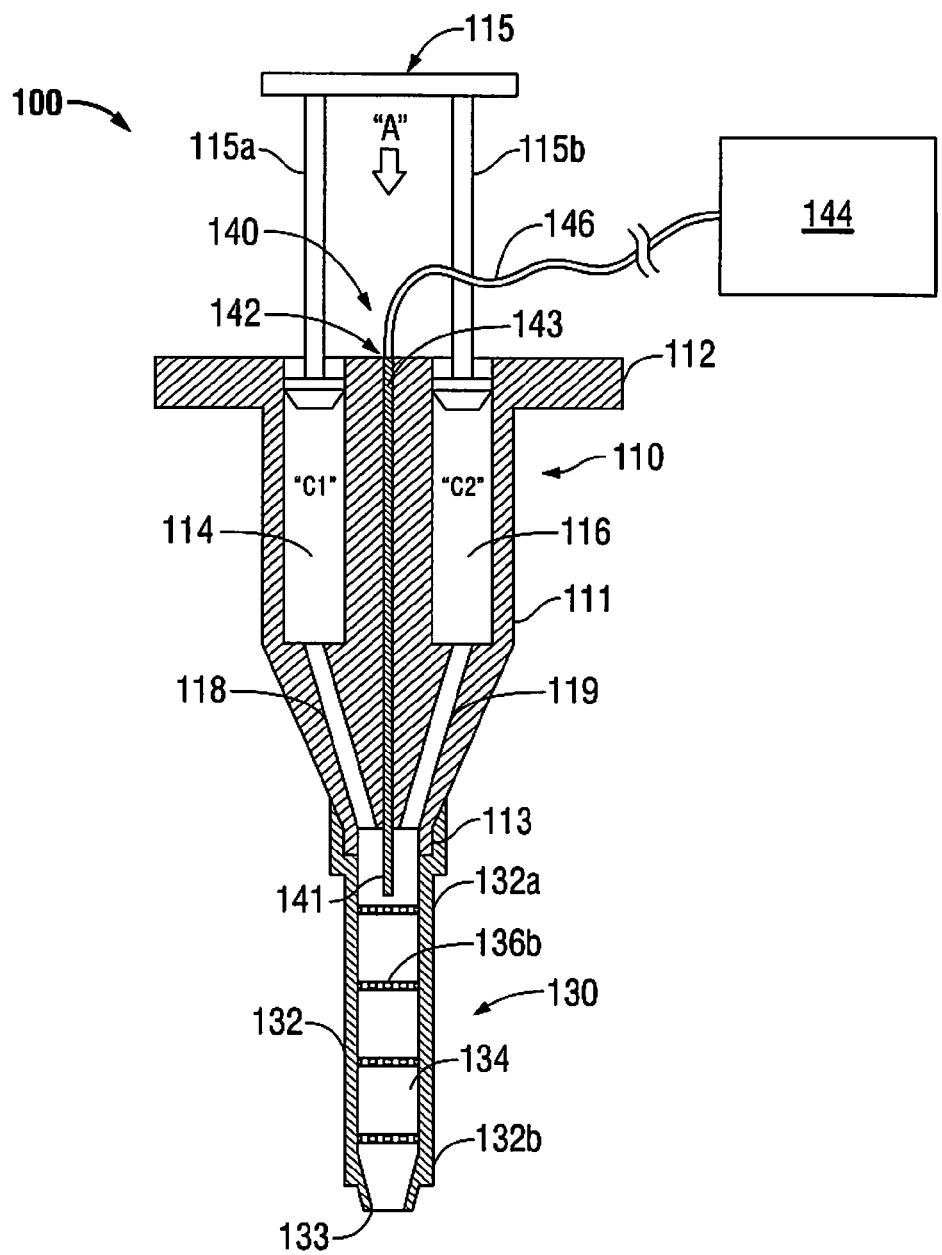
FIG. 3A is a cross-sectional view of the apparatus of FIG. 1 including another embodiment of mixing elements in accordance with the present disclosure.
Figure 3B:
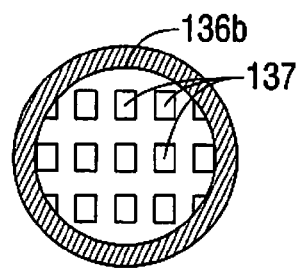
FIG. 3B is a front cross-sectional view of a mixing element of FIG. 3A.

In another illustrative embodiment as shown in FIGS. 3A-3B, mixing assembly 130 may includes one or more mixing elements 136b extending radially across mixing cavity 134 and define substantially screen-like members. Mixing elements 136b include a plurality of openings 137 extending therethrough to permit the flow of first and second components "C1", "C2", or a mixture thereof, through mixing elements 136b. The size and number of mixing elements 136b, as well as the size and number of openings 137 within mixing element 136b, may be varied depending on the components being mixed and the desired properties of the resulting mixture.

Figure 4:
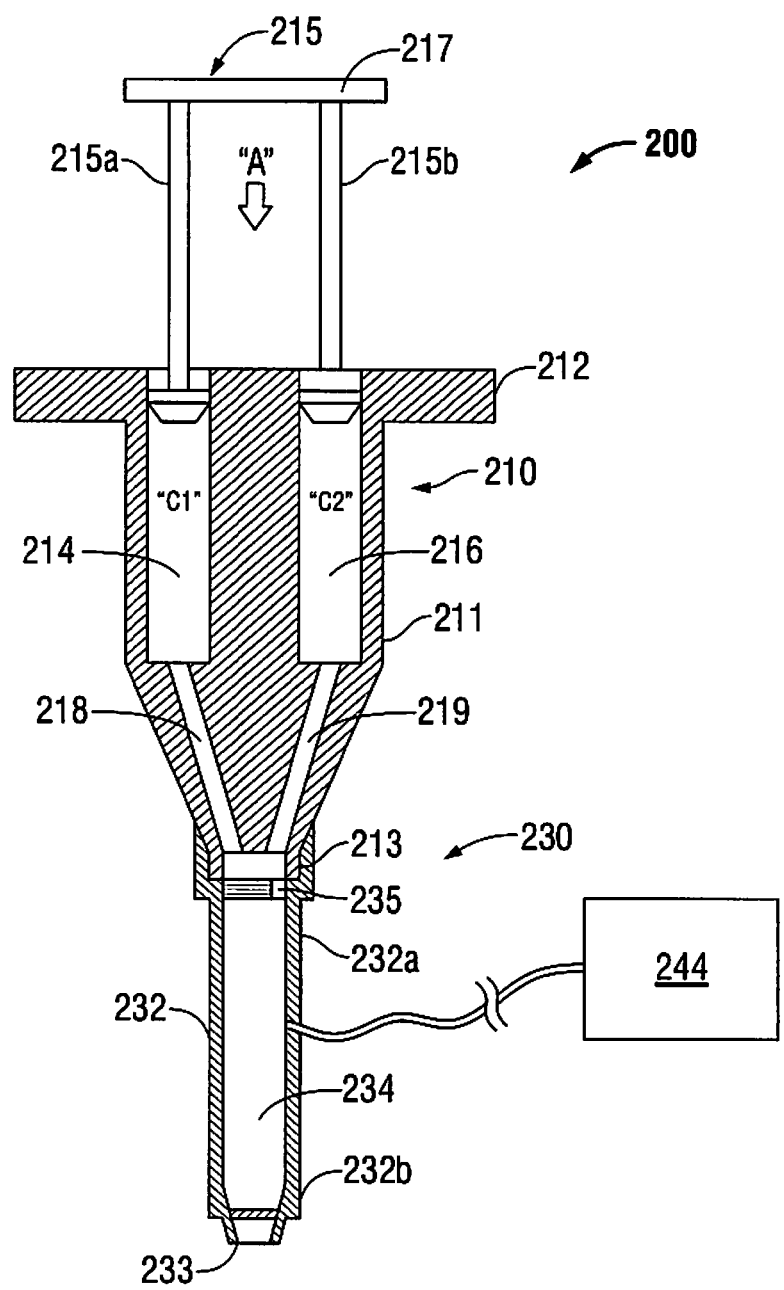
FIG. 4 is a cross-sectional view of an alternative embodiment of an apparatus for mixing and catalyzing first and second precursors to form medical devices in accordance with the present disclosure.

With reference now to FIG. 4, an alternative embodiment of the present disclosure is shown generally as applicator 200. Applicator 200 is substantially similar to applicator 100 and will therefore only be described as related to the differences therebetween. Supply assembly 210 includes first and second component syringes 214, 216 operably connectable to a housing 211. First and second component syringes 214, 216 are operably connectable by a flange member 212 and each include first and second plunger members 215a, 215b, respectively, for selectively dispensing respective first and second components "C1", "C2" therefrom. Supply assembly 210 further includes a plunger cap member 217 configured to fit about an end of first and second plunger member 215a, 215b. In this manner, first and second plunger members 215a, 215b may be depressed uniformly, thereby dispensing equal amounts of first and second components "C1", "C2" from respective first and second component syringes 214, 216.

With reference still to FIG. 4, mixing assembly 230 includes an elongate member 232 having a substantially closed proximal end 232a, a substantially closed distal end 232b, and a mixing cavity 234 extending therebetween. Proximal end 232a of mixing assembly 230 includes a snap fitting for operable connection with extension 213 of housing 211 and includes an inlet 235 for introducing components "C1", "C2" from supply assembly 210. Distal end 232b of mixing assembly 230 defines an outlet 233 configured for dispensing the mixture of first and second components "C1", "C2". A microwave generator 244 is coupled to the elongated member 232 such that the mixing cavity 234 forms a substantially closed reactor for irradiating first and second components "C1", "C2".

In embodiments, the mixing cavity may include a coating containing a catalyst to aid in the reaction of first and second components "C1", "C2". The coating may include any number of substances capable of maintaining and exposing a catalyst to first and second components "C1", "C2", or a mixture thereof, without contaminating first and second components "C1", "C2" or the mixture thereof with the catalyst, such as a chelating resin. In embodiments, a metal catalyst, such as a transition metal, may be utilized to aid in polymerization of the first and second components into the injectable medical device. Metals and transition metal catalysts which may be utilized include, for example, copper, zinc, iron, aluminum, magnesium, and alloys thereof. In embodiments, a metal or transition metal ion catalyst may be present on one or more surfaces of the apparatus using a chelating matrix of the type used in immobilized metal affinity chromatography. For example, a suitable chelating matrix can be prepared by derivatization of hydroxyl groups with iminodiacetic acid (IDA), carboxymethyl aspartic acid (CM-Asp) and with tris(carboxymethyl)ethylenediamine (TED) on agarose beads, as well as silica gel functionalized with IDA. The preparation of such chelating matrices is disclosed in Le Dévédec et al., "Separation of chitosan oligomers by immobilized metal affinity chromatography," *J Chromatogr A.*, 2008 Jun. 20; 1194(2):165-71, the entire disclosure of which is incorporated herein by this reference.

The substance used as a coating corresponds to the material needed to catalyze the resulting mixture. All or a portion of the mixing cavity may be covered in a coating. All or a portion of the surface of mixing elements (e.g., mixing elements 136a of FIG. 2 or 136b of FIGS. 3A and 3B) may be covered in a coating. In this manner, as first and second components "C1", "C2" flow into and through the mixing cavity and optionally pass through the mixing elements, the first and second components "C1", "C2", and the resulting mixture, are exposed to the catalyst maintained within coating. Contact of first and second components "C1", "C2", and the resulting mixture, with the coating on the mixing element(s) and/or the surface of mixing cavity, in combination with the microwave energy, catalyzes the resulting mixture.

The injectable compositions of the present disclosure can be used for a number of different human and animal medical applications including, but not limited to, wound closure (including surgical incisions and other wounds), sealants, adhesion barriers, and other implantable devices. Adhesives may be used to bind tissue together either as a replacement of, or as a supplement to, sutures, staples, clamps, tapes, bandages, and the like. Use of the present compositions can eliminate or substantially reduce the number of sutures normally required during current practices, and eliminate the subsequent need for removal of staples and certain types of sutures. The compositions described herein can thus be suitable for use with delicate tissues where sutures, clamps or other conventional tissue closure mechanisms may cause further tissue damage. For example, the compositions of the present disclosure may be used to seal or adhere delicate tissue together in place of conventional tools that may cause mechanical stress. The present compositions can also be used to seal air and/or fluid leaks in tissue as well as to prevent post-surgical adhesions and to fill voids and/or defects in tissue.

For example, to effectuate the joining of two tissue edges, the two edges may be approximated, and an injectable composition of the present disclosure may be applied to the two approximated edges with a mixing applicator as described above. A second tissue surface may then be contacted with the tissue possessing the composition so that it adheres thereto.

The compositions described herein can also be used as sealants. When used as a sealant, a composition of the present disclosure can be used in surgery to prevent or inhibit bleeding or fluid leakage both during and after a surgical procedure. It can also be applied to prevent air leaks associated with pulmonary surgery. Compositions herein may be applied directly to the desired area in at least an amount sufficient to seal off any defect in the tissue and seal off any fluid or air movement. The compositions may also be used to prevent or control blood or other fluid leaks at suture or staple lines.

The composition of the present disclosure may crosslink rapidly, in embodiments, in less than one minute. Compositions of the present disclosure can thus be applied to the wound and allowed to set, thereby closing the wound.

The present compositions also can be used to attach skin grafts and position tissue flaps during reconstructive surgery. Alternatively, the present compositions can be used to close tissue flaps in periodontal surgery.

In another embodiment, the present disclosure is directed to a method for using compositions of the present disclosure to adhere a medical device to tissue. Suitable medical devices include implants. Other medical devices include, but are not limited to, pacemakers, stents, shunts and the like. Generally, for adhering a device to the surface of animal tissue, a composition of the present disclosure can be applied to the device, to the tissue surface, or to both. The device and tissue surface are then brought into contact with the present composition therebetween. In other embodiments the first component may be applied to the device or tissue surface, and the second component applied to the other. The device and tissue surface are brought into contact with each other, so that the first component and second component are in contact with each other. Application of the catalyst will result in formation of a composition of the present disclosure. Once the composition crosslinks and sets, the device and tissue surface are effectively adhered to each other.

The present compositions can also be used to prevent post surgical adhesions. In such an application, a composition of the present disclosure may be applied and cured to form a layer on surfaces of internal tissues in order to prevent the formation of adhesions at a surgical site during the healing process.

The resulting injectable compositions have a number of advantageous properties. The compositions of the present disclosure are safe, possess enhanced adherence to tissue, are biodegradable, have enhanced hemostatic potential, have low cost, and are easy to prepare and use. By varying the selection of the compounds utilized to form the composition, the strength and elasticity of the composition can be controlled, as can the gelation time.

Adhesives and/or sealants formed with compositions of the present disclosure possess excellent strength and similar physical properties. The compositions herein rapidly form a compliant gel matrix, which insures stationary positioning of tissue edges or implanted medical devices in the desired location and lowers overall required surgical/application time. The composition forms strong cohesive bonds. It exhibits excellent mechanical performance and strength, while retaining the necessary pliability to adhere living tissue. This strength and pliability allows a degree of movement of tissue without shifting the surgical tissue edge.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described, as modifications and variations are intended to come within the scope and spirit of the claims appended hereto.

What is claimed is:

1. An apparatus comprising:
   a supply assembly configured to maintain and selectively dispense a first precursor functionalized with a first reactive member and a second precursor functionalized with a second reactive member;
   a mixing assembly configured to mix the first and second precursors in a mixing cavity defined therein; and
   at least one source of microwave energy configured and adapted to irradiate the mixed first and second precursors within the mixing cavity, wherein the source of microwave energy includes a microwave generator operably coupled to a microwave antenna, the microwave antenna including a radiating section disposed within the mixing cavity.

2. The apparatus of claim 1, wherein the mixing cavity is configured as a substantially closed reactor for receiving microwave energy from a microwave generator.

3. The apparatus of claim 1, wherein the mixing cavity includes a mixing element.

4. The apparatus of claim 3, wherein the mixing element comprises a static mixer including substantially fixed helical members extending along a length of the mixing cavity.

5. The apparatus of claim 3, wherein at least a portion of the mixing element includes a coating containing a catalyst.

6. The apparatus according to claim 3, wherein the radiating section of the microwave antenna is disposed proximal to the mixing element in the mixing cavity.

7. The apparatus of claim 1, wherein at least a portion of the mixing cavity includes a coating containing a catalyst.

8. The apparatus of claim 7, wherein the catalyst is a metal ion.

9. The apparatus of claim 8, wherein the metal ion is a transition metal ion.

10. The apparatus of claim 1, wherein the source of microwave energy emits microwave energy at a frequency from about 300 MHz to about 20,000 MHz.

11. The apparatus according to claim 1, wherein the first precursor possesses an azide group and the second precursor possesses an alkyne group.

12. The apparatus according to claim 1, wherein the first precursor and optionally the second precursor comprises a polyol core.

13. The apparatus according to claim 12, wherein the polyol is selected from the group consisting of polyethers, polyesters, polyether-esters, polyalkanols, and combinations thereof.

14. The apparatus according to claim 1, wherein the microwave antenna passes through the supply assembly.

15. The apparatus according to claim 14, wherein the radiating section of the microwave antenna is disposed in a proximal end of the mixing cavity.

* * * * *